United States Patent
Prabhune et al.

(10) Patent No.: US 6,379,937 B1
(45) Date of Patent: Apr. 30, 2002

(54) PROCESS FOR THE PREPARATION OF A MIXTURE OF 19 HYDROXYELCOSATETRAENOIC ACID AND 20 HYDROXYEICOSATETRACNOIC ACID (10 HETE AND 20 HETE)

(75) Inventors: Asmita Ashutosh Prabhune, Pune (IN); Colin Ratledge, Beverley (GB)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/739,727

(22) Filed: Dec. 18, 2000

(51) Int. Cl.[7] .............................. C12P 7/64; C12P 7/40; C12P 1/02
(52) U.S. Cl. .................. 435/134; 435/136; 435/171; 435/177; 435/247; 435/249; 435/255.4; 435/256.8
(58) Field of Search .................................. 435/134, 136, 435/171, 249, 247, 255.4, 177, 256.8

(56) References Cited

U.S. PATENT DOCUMENTS

| 4,867,915 | A | * | 9/1989 | Muchwoski et al. | 514/522 |
| 5,897,994 | A | * | 4/1999 | Sandoz et al. | 435/134 |
| 6,075,183 | A | * | 6/2000 | Knutzon et al. | 435/134 |
| 6,140,364 | A | * | 10/2000 | Falck et al. | 514/552 |

* cited by examiner

*Primary Examiner*—Herbert J. Lilling
(74) *Attorney, Agent, or Firm*—Morgan & Finnegan, L.L.P.

(57) ABSTRACT

The present invention relates to a novel process for the preparation of mixture of 19 hydroxyeicosatetraenoic acid and 20 hydroxyeicosatetraenoic acid (19 HETE and 20 HETE) by biotransformation of Arachidonic acid or Poly Unsaturated Fatty Acids (PUFA) with yeast as the biotransforming agent.

16 Claims, No Drawings

ованnoic acid
PROCESS FOR THE PREPARATION OF A MIXTURE OF 19 HYDROXYELCOSATETRAENOIC ACID AND 20 HYDROXYEICOSATETRACNOIC ACID (10 HETE AND 20 HETE)

FIELD OF THE INVENTION

The present invention provides a novel process for preparation of a mixture of 19 hydroxyelcosatetraenoic acid (19, HETE) and 20 hydroxyeicosatetracnoic acid (20 HETE).

BACKGROUND

Arachidonic acid metabolites obtained from three enzymatic pathways are known to be vasocative. A variety of cytochrome P450 metabolites affect vascular tone, including the ω-hydroxylate products 19 HETE and 20 HETE. 20 HETE derived from arachidonic acid is released from activated neutrophilis and contribute to vascular tone, in number of organ systems. Zou et al. in 1994 have reported that inhibitors of renal vascular 20 HETE production impairs autoregulation of blood flow. Ma in 1993 have shown that 20 HETE is an endogenous vasoconstrictor of canine renal arcuate arteries, where as Escalante in 1993 has shown 20 HETE as an endothelium dependent vasoconstrictor in rabbit arteries. Pratt et al. in 1998 have reported 20 HETE is a potent vasodilator of bovine coronary arteries. It also contributes to vascular tone in a number of organ systems, such as aorta, mesentric, cortical and renal arteries. They also report that bovine arteries when incubated with 20 HETE produce prostacyclin in response to increasing concentration of 20 HETE. Furthermore, 20 HETE was shown to activate MAPK (mitogen activated protein kinase) which amplifies $CPLA^2$ (cytosolic phosopholipase $A^2$) activity and releases additional arachidonic acid by positive feed back mechanism which might play a role in signaling processes involved in inflammation, in cell growth, proliferation and differentiation. Schwartzmann in 1988 has shown 19(s) HETE may contribute to the regulation of renal function by regulating $Na^+$—$K^+$ ATPase which is essential for transtubular transport processes. There are no reports till date for microbial transformation of 20 HETE and 19 HETE from extraneously added arachidonic acid. The reports of 20 HETE production are either by incubating arachidonic acid with mammalian cells or by totally synthetic forms. Most of the reported transformation involve oxidation of activated carbon (allylic), but oxidation of unactivated carbon is very difficult even by chemical methods. This is due to lack of reactivity at this terminal carbon. One of the chemical methods for production of 19 HETE described by Schwartzmann et al., 1988 is as follows to a vigorously stirring −40° C. solution of methyl 14–15 DHET (130 mg 0.369 mmole) in dichloroethane (4 ml) were added powdered, anhydrous sodium bicarbonate (40 mg, 0.387 mmole) and lead tetracaetate (171.6 mg 0.387 mmole). After 20 minutes the reaction mixture was passed rapidly through a silica gel bed and the filter cake was washed with dry ether (10 ml). The combined organic filtrates were concentrated under reduced pressure on a rotary evaporator. The resultant oily aldehyde was used directly in the next reaction after drying azeolropically with benezene n-Butyllithium (0.42 ml) was added dropwise with stirring to a −78° C. solution 5 (R)-(t-butyldiphenyl sililoxy) hexyltriphenylphosphonium bromide in anhydrous THF (4 ml) under argon. After 45 minutes, a THF (2 ml) solution of above aldehyde was added slowly followed after 2 minutes by dry hexamethylphosporamide (1.5 ml). The reaction mixture was warmed over 0° C., poured into 25% aqueous ammonium acetate and extracted with ethyl acetate (0.4×10 ml). The combined organic extracts were washed with water, brine and dried over sodium sulphate. Concentration and purification of the residue was done on silica gel colurnn. Yield was approximately 37%.

Biological methods require mammalian cells which are tedious and expensive, and the productivity is very low. One of the methods described by Escalante in 1989 is as follows: 20 HETE is prepared by incubating rate renal cortical microsomes (3 mg) with arachidonic acid in presence of NADPH and indomethacin. Separate and purified by reverse and normal phase liquid chromatography as described by Schwartzmann in 1988. For this rat aortic rings, male Sprague Dawley rats (300–350 g) were killed by cervical dislocation and thoracic aorta was carefully removed and placed into cold Kreb's bicarbonate buffer freed of periadventitial fat and cut into 3–4 mm wide rings. To ensure the integrity of the vascular endothelium, care was taken during the dissection to avoid stetching or contact of instrument with the luminal surface of the ring. The aortic rings were mounted in 5 ml of water jacketed organ bath maintained at 37°0 C. and equilibrated for 1.5–2 hrs. in Kreb's bicarbonate buffer gassed with 95% $O_2$ and 5% $CO_2$. The composition of the Kreb's bicarbonate buffer was (g/l) NaCl 6.95; KCl 0.354; $CaCl_2$ 0.280; $KH_2PO_4$ 0.162; $MgSO_4$, 7 $H_2O$ 0.294, NaHCO, 2.1 and dextrose 2.0. A minimum of four rings was used simultaneously from each aorta. Basal tone was set at 2 g and adjusted accordingly over the equilibrium period. Tension was measured using glass model RPS 7C8A. This procedure provided optimal conditions for reproducible isomatic force development.

There are always side products formed hence purification of the desired end product increases cost of the metabolite (Sigma price of 10 $\mu$gs of 20 HETE is 78 $).

OBJECTS OF THE INVENTION

The main object of the present invention is to provide a novel process for preparation of a mixture of 19 hydroxyeicosatetraenoic acid and 20 hydroxyeicosatetraenoic acid (19 HETE and 20 HETE).

Another object of the invention is to provide one step transformation of arachidonic acid to a mixture of 19 HETE and 20 HETE as compared to the 10 step process of the prior art (Falck et al., 1988).

Still another object of the present invention is to provide a process for the hydroxylation which is stereo specific, in case of 19 HETE.

Yet another object of the present invention is to provide a process wherein the conversion efficiency of Arachidonic acid to 19 HETE and 20 HETE is 100 times higher than that of mammalian cells as there are only two metabolites formed and they are to metabolized further. In chemical as well as biological methods the yield is ver low and in picomoles whereas microbial transformation has shown in milligrams levels. Yet another object is to provide a process for preparation of mixture of 19 hydroxyeicosatetraenoic acid and 20 hydroxyeicosatetraenoic acid (19 HETE and 20 HETE) in which yeast cells require less restricted conditions and cheaper carbon sources such as molasses, cornsteep liquor etc., than mammalian cells or isolated P 450 from mammalian cells.

Yeast cells are grown in conventional medium, containing glucose as carbon source with moderate temperature at 30°0 C. and other conditions, whereas in chemical methods for preparation of the same requires temperature ranging from

DETAILED DESCRIPTION OF THE INVENTION

Accordingly, the present invention provides a process for the preparation of mixture of 19 hydroxyeicosatetraenoic acid and 20 hydroyeicosatetraenoic acid (19 HETE and 20 HETE) which comprises the steps of growing yeast species such as *Canadian apicola* (ATCC 96134, ATCC 24616) (Isolated from intestine of bee Ref: Antoinie Van Leeuwenhoek, 24 18, 1958) or *Candida bombicola* (ATCC 22214) (formerly known as Torulopsis bombicola isolated from Bumblebee honey. Ref: Agr. Biol. Chem, 44.221–2223, 1980 and Biotch.Lett 6,225–230, 1984) (i.e. yeast species) in a conventional growth medium consisting of carbon, nitrogen sources and other micro-ingredients supplemented with arachidonic acid or Poly Unsaturated Fatty Acids (PUFA) for a period of 12 to 96 hrs., in a known manner, separating the biomass from the medium (broth), by conventional methods, extracting the separated broth with an organic solvent, drying by conventional method, hydrolyzing by conventional method or by enzymatic hydrolysis to obtain 19 HETE and 20 HETE. These microorganisms used in the invention i.e. *Candida apicola* (ATCC 96134, ATCC 24616) or *Candida bombicola* (ATCC 22214) are publicly available without any difficulty and there is no difficulty in securing samples of these microorganisms.

In one of the embodiments of the present invention, arachidonic acid or an oil containing polyunsaturated fatty acids is added to the medium at the time of the inoculation of the yeast sp or added after a period of growth.

In another embodiment the Poly Unsaturated Faty Acids (PUFA) may be such as linoleic acid, alpha and gamma linolenic acid, dibromo gamma linolanic acid eicosapentaenoic, docosa pentaenoic acid (20:5, n-6 and 20:5, n-3) and docadthexacnoic acid.

In still another embodiment the concentration of the arachidonic acid or PUFA may be ranging between 10 mg to 5000 mg/lit of the medium either by single addition or by programmed additional (dose dependent).

In another embodiment the solvent used for supplementing of arachionic acid or PUFA may be alkanols preferably ethanol or by direct addition of arachidonic acid or by addition of methyl or ethyl esters of arachidonic acid.

In another embodiment the solvent used for extraction of the mixture of products may be polar solvents exemplified by but not limited to ethyl acetate, chloroform, n-hexane preferably ethyl acetate.

In a feature of the present invention the mixture of the 19 hydroxyelcosatetraenoic acid and 20 hydroxyeicosatetraenoic acid and 20 hydroxyeicosatetraenoic acids may be separated to free hydroxy fatty acids by acid hydrolysis effected by using mineral acid such as molar (dilute) HCL, $H_2SO_4$ and nitric acid.

In a feature of the present invention, the mixture of the conjugated 19 hydroxyeicosatetraenoic acid and 20 hydroxyeicosatetraenoic acids may be separated to free fatty acids by enzymatic hydrolysis and effected by using β-glucosidase or by similar enzymes.

In yet another feature of the present invention, the conventional media composition of the fermentor medium may be as given in Tables 1 & 2.

TABLE 1

| The medium of growth as well as fermentation consisted of (gl[1]) | |
|---|---|
| Glucose | 10–100 |
| Yeast Extract | 0.2–1.0 |
| Ammonium sulphate | 1.0–0.8 |
| MgSO$_4$ 7H$_2$O | 0.1–0.3 |
| Na$_2$IIPO$_4$ | 0.2–2.0 |
| KH$_2$PO$_4$ | 0.7–7.0 |
| pH | 5.5 |

TABLE 2

| The medium of growth as well as fermentation consisted of (g/l) | |
|---|---|
| Glucose | 1.0–10 |
| Yeast Extract | 0.3–3.0 |
| Malt Extract | 0.3–3.0 |
| Peptone | 0.5–5.0 |
| pH | 5.5 |

In yet another feature of the present invention the yeast used may be optionally immobilized by conventional methods like using calcium alginate. The use of immobilized yeast enables continuous production.

The process of the present invention is described hereinbelow with reference to examples, which are illustrative in nature and should not be construed to limit the scope of the present invention in any manner.

EXAMPLE 1

The 19 HETE and 20 HETE were obtained from hydrolysis of the sophorolipid isolated from the fermentation of *Candida apicola* ATCC 24616 or *Candid bombicola* ATCC 22214.

50 mg of arachidonic acid in 5 ml of ethanol is added during inoculation. For the fermentation experiment cells were precultivated on medium as described above in a 250 ml flask containing 50 ml medium at 30° C. and 150 iprn. Late logarithmic cells (24 h) were used as an inoculum. These starter cultures (4–6×10$^6$ cells /ml) were used to inoculate conical flask (11) each containing 400 ml fermentation medium. Crude sophorolipid was extracted after 96 hrs. Sophorolipid was purified as described previously (Hommel et al 1987). Crystalline crude sophorolipid was washed three times with n hexane (20 ml×3) to remove residual substrate and dissolved in minimum volumes of (1–3 ml) chilled ethyl acetate. The solvent was removed under reduced pressure and the resulting yellowish glycolipid was used as a substrate for acid hydrolysis. Acid hydrolysis was done essentially as described by Hommel, (1987) which is as follows, 20 mg of sophorolipid was hydrolysed with 1 ml of 1 M HCl in a boiling water bath for 2 hrs. The liberated fatty acids were extracted with chloroform.

EXAMPLE 2

This example illustrates addition of arachidonio acid in the range of 10 mg to 5000 mg in different flasks where arachidonic acid was dissolved in ethanol or added directly in to the medium. All other conditions were same as described in Example 1.

EXAMPLE 3

This example illustrates addition of arachidonic acid in acid form. 1000 mg of arachidonic acid was added in precultivated cells of yeast or in growing phase in proportion to the weight of the cells. Collection of sophorolipid and hydrolysis was carried out as described in Example 1.

EXAMPLE 4

This example illustrates hydrolysis of sophorolipid by enzyme β-glucosidase. 2–10 mgs of sophorolip was dissolved in 50 mM potassium phosphate buffer pH 7.10 U of the enzyme was added into this solution and incubated for 1 hour and the supernatant was used for extraction of free hydroxy fatty acids.

EXAMPLE 5

This example illustrates the purification of the products by fractionation on 500 mg Aminopropyl Sep—Pak Cartridges (Waters) by modification of the method described by Kaluzny et al (1985). Samples (0.5 ml chloroform) were applied to the cartridges which have been equilibrated with 5 ml hexane. Neutral lipids were eluted from the column with 25 ml chloroform /2-propanol (2.1, v/v). Monohydroxylated fatty acids were eluted from the column with 25 ml of 2% acetic acid in diethyl ether. Polar fatty acids were eluted with 25 ml of methanol. Ether fractions were rotary evaporated and the residues were taken in a minimum volume (0.5 ml) of chloroform and were separated on TLC (Keiselgel G60).

EXAMPLE 6

This example illustrates the confirmation of formation of end products. Methylated and silylated samples (1 μl) were analyzed by gas liquid chromategraphy equipped with a flame ionization detector (FID). Separation of fatty acid derivatives was achieved using BP-1 fused silica capillary column (25 m×0.22 mm with 0.25 mm coating) with $N_o$ as the carrier gas. The temperature was initially 220° C. and an initial time of 5 min. which reached a final temperature at 280° C. at ramp rate 2° C/min.

EXAMPLE 7

Methylated and silylated samples were identified on GC.MS. Gas liquid chromatography in combination with mass spectrometry was carried out with Finnegan Series automated quadruple mass spectrometry equipped with a BP-5 fused silica column (30 m×0.25 mm with 0.25 mm coating). Parameters for gas liquid chromatography were: He carrier gas at 0.14 arm head pressure; 10.1 split; injector temperature, 240° C.; initial temperature, 220° C. initial time, 5 min; ramp rate 5° C. $min^{-1}$ final temperature, 280° C.; final time 10 min, injection volume; 1μ. Mass spectroscopy parameters were: source temperature 240° C.; manifold temperature 100° C., ionization current, 3.0 nm, scan range 70 to 650 atomic mass units in 1 scan. Results were confirmed with authentic standards.

The main advantages of the present invention are:
1. There is no reported method by which 19 HETE and 20 HETE can be prepared by microbial transformation.
2. In present method we report for biotransformation of Arachidonic acid into 19 HETE and 20 HETE.
3. In present method we also report that the given culture can hydroxylate other Poly Unsaturated Fatty Acids such as arachidonic acid, linolenic acid (alpha and gamma) linoleic acid, eicosapentaenoic acid (EPA), docosapentacnoic acid (DPA), stearadonic acid (18:4) and docosahexaenoic acid (DHA) into respective α-I hydroxylated products.
4. In the present invention we also report for the simpler method for production of 19 HETE and 20 HETE.
5. Another advantage of the invention is there are no other side products from arachidonic acid other than 19 HETE and 20 HETE.
6. Advantage of the invention is, since there are only two end products from arachidonic acid, purification procedure is simpler and easier economic. (Does not involve many steps).
7. Another advantage of the invention is, as biotransforming agent is yeast, it is easier to handle the system than mammalian cells. (operates in mild conditions0.
8. Another advantage is yeast can be grown on cheaper carbon source such as molasses keeping the end product value minimum.
9. This is very important as till today this is produced either by purely chemical method (multi-steps and hazardous) or incubating arachidonic acid with mammalian cells. This invention is eco-friendly as hydrolysis of the sophorolipid is achieved by enxymatic hydrolysis (Green Technology) as most of the enzymatic reactions are carried out in aqueous medium and all other moderate conditions.
10. Another advantage of the present invention is use of immobilized system for continuous conversion of arachidonic acid (or any other PUFA) into bio-active compounds such as 19 HETE and 20 HETE.
11. Another advantage of the present invention is that it offers manual activation at normally reactive carbon centres where no conventional chemistry is applicable.

What is claimed is:

1. A process for the preparation of a mixture of 19 hydroxyeicosatetraenoic acid and 20 hydroxyeicosatetraenoic acid (19 HETE and 20 HETE), which comprises:
   (a) growing *Candida apicola* (ATCC 96134 and ATCC 24616) or *Candida bombicola* (ATCC 22214) in a growth medium comprising carbon and nitrogen sources supplemented with one or more Poly Unsaturated Fatty Acids (PUFA) for a period of 12 to 96 hrs to form a biomass,
   (b) separating the biomass from the medium (broth),
   (c) extracting the separated broth with an organic solvent, and
   (d) drying and hydrolyzing the extract to obtain 19 HETE and 20 HETE.

2. A process as claimed in claim 1 wherein the one or more poly unsaturated fatty acids (PUFA) are selected from the group consisting of linoleic acid, alpha and gamma linolenic acid, dibromo gamma linolenic acid, steradonic acid (18–4), arachidonic acid, eicosapentaenoic acid, docodahexaenoic acid and docosapentaaenoic acid.

3. A process as claimed in claim 1 wherein the concentration of the PUFA ranges between 10 mg to 5000 mg/lit of the medium.

4. A process as claimed in claim 1 wherein the PUFA used are in the form of a solution of an alkanol.

5. A process as claimed in claim 1 wherein the organic solvent used for extraction of the mixture of products is selected from the group of solvents consisting of ethyl acetate, chloroform, and n-hexane.

6. A process as claimed in claim 1 wherein the hydrolysis is carried out with a mineral acid selected from the group consisting of (dilute) HCl, $H_2SO_4$ and nitric acid.

7. A process as claimed in claim 1 wherein the hydrolysis is carried out by enzymatic hydrolysis.

8. A process as claimed in claim 1 wherein the growth medium is selected from the compositions as shown hereinbelow:

| (A) | |
|---|---|
| Glucose | 10–100 g/l$^{-1}$ |
| Yeast Extract | 0.2–1.0 g/l |
| Ammonium sulphate | 1.0–0.8 g/l |
| MgSO$_4$ 7H$_2$O | 0.1–0.3 g/l |
| Na$_2$HPO$_4$ | 0.2–2.0 g/l |
| KH$_2$PO$_4$ | 0.7–7.0 g/l |
| pH | 5.5 g/l | and

| (B) | |
|---|---|
| Glucose | 1.0–10 g/l |
| Yeast Extract | 0.3–3.0 g/l |
| Malt Extract | 0.3–3.0 g/l |
| Peptone | 0.5–5.0 g/l |
| pH | 5.5 g/l. |

9. A process as claimed in claim 1 wherein the yeast is optionally immobilized by using calcium alignate.

10. A process as claimed in claim 1 wherein the PUFA used includes arachidonic acid.

11. A process as claimed in claim 1 wherein the PUFA used is arachidonic acid.

12. A process as claimed in claim 1 wherein the PUFA used are in the form of a methyl or ethyl ester derivative of arachodonic acid.

13. A process as claimed in claim 4 wherein the alkanol used is ethanol.

14. A process as claimed in claim 5 wherein the organic solvent used is ethyl acetate.

15. A process as claimed in claim 7 wherein the enzymatic hydrolysis is carried out using glucosidase.

16. A process as claimed in claim 3 wherein the PUFA is arachidonic acid. medium.

* * * * *